United States Patent [19]
Purola et al.

[11] Patent Number: 6,113,262
[45] Date of Patent: Sep. 5, 2000

[54] APPARATUS FOR TESTING ELECTRICAL COMPONENTS

[75] Inventors: David Purola, Commerce; David A. Klecha, Taylor, both of Mich.

[73] Assignee: TRW Inc., Lyndhurst, Ohio

[21] Appl. No.: 09/235,873

[22] Filed: Jan. 22, 1999

[51] Int. Cl.[7] ................................................ G01N 25/00
[52] U.S. Cl. .............................. 374/45; 73/865.6; 374/57
[58] Field of Search ................................. 374/45, 4, 57, 374/50, 5; 165/201; 73/865.6

[56] References Cited

U.S. PATENT DOCUMENTS

| | | | |
|---|---|---|---|
| 4,159,171 | 6/1979 | Nineberg | 354/307 |
| 4,519,718 | 5/1985 | Staffin et al. | 374/45 |
| 4,729,246 | 3/1988 | Melgaard et al. | 374/57 |
| 4,779,163 | 10/1988 | Bickford et al. | 374/57 |
| 4,871,965 | 10/1989 | Elbert et al. | |
| 5,039,228 | 8/1991 | Chalmers | 374/57 |
| 5,167,451 | 12/1992 | Müller et al. | 374/57 |
| 5,193,910 | 3/1993 | Kinoshita | 374/45 |
| 5,431,491 | 7/1995 | Melgaard et al. | |

FOREIGN PATENT DOCUMENTS

| | | | |
|---|---|---|---|
| 405296636 | 8/1978 | Japan. | |
| 0274035 | 11/1989 | Japan | 374/45 |
| 404355345 | 12/1992 | Japan | 374/57 |
| 0619828 | 8/1978 | U.S.S.R. | 73/865.6 |

*Primary Examiner*—Diego Gutierrez
*Assistant Examiner*—Lydia M. DeJesús
*Attorney, Agent, or Firm*—Tarolli, Sundheim, Covell, Tummino & Szabo L.L.P.

[57] ABSTRACT

An apparatus (10) for testing at least one article (160) comprises a first chamber (20) having a controllable first environment, a second chamber (30) having a controllable second environment, and an intermediate housing (40) connected between the first and second chambers. The intermediate housing (40) defines a work space (54) and includes a window (70) which provides access to the work space. A rotatable container (100) is disposed in the work space (54) and defines a test chamber (110) in which the at least one article (160) is placed. The container (100) is rotatable between a first position in which the test chamber (110) is exposed to the first environment and is thermally insulated from the second environment, a second position in which the test chamber (110) is exposed to the second environment and is thermally insulated from the first environment, and a third position in which the test chamber (110) is accessible through the window (70) in the intermediate housing (40).

19 Claims, 2 Drawing Sheets

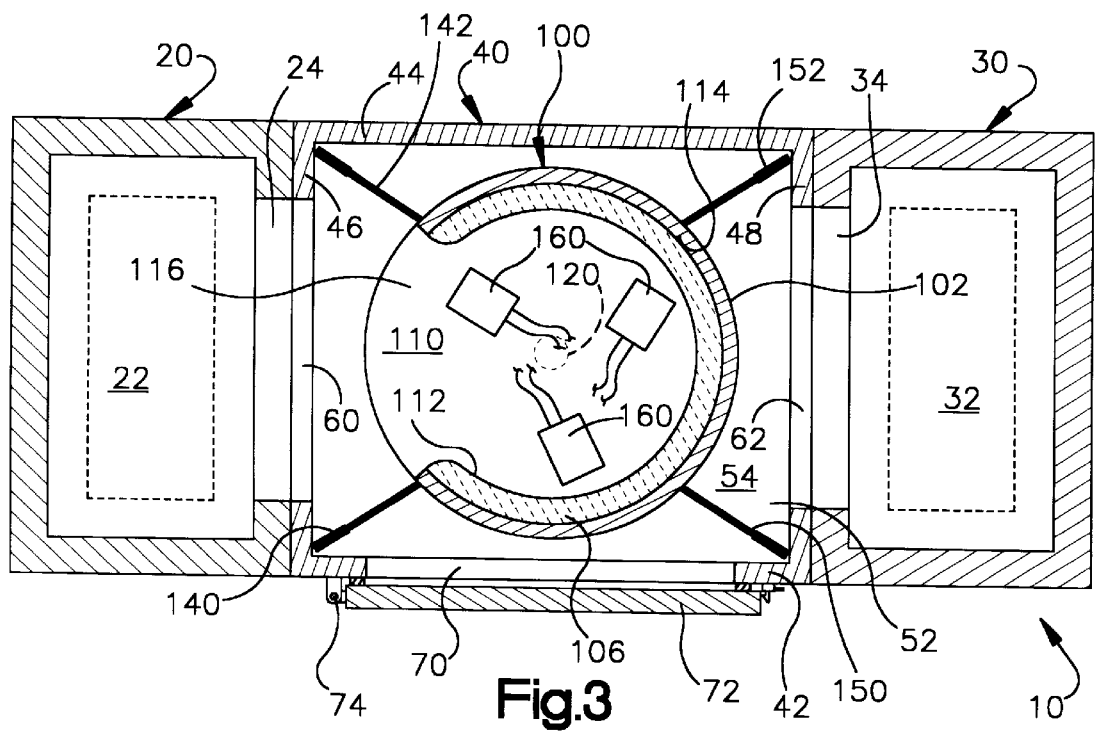
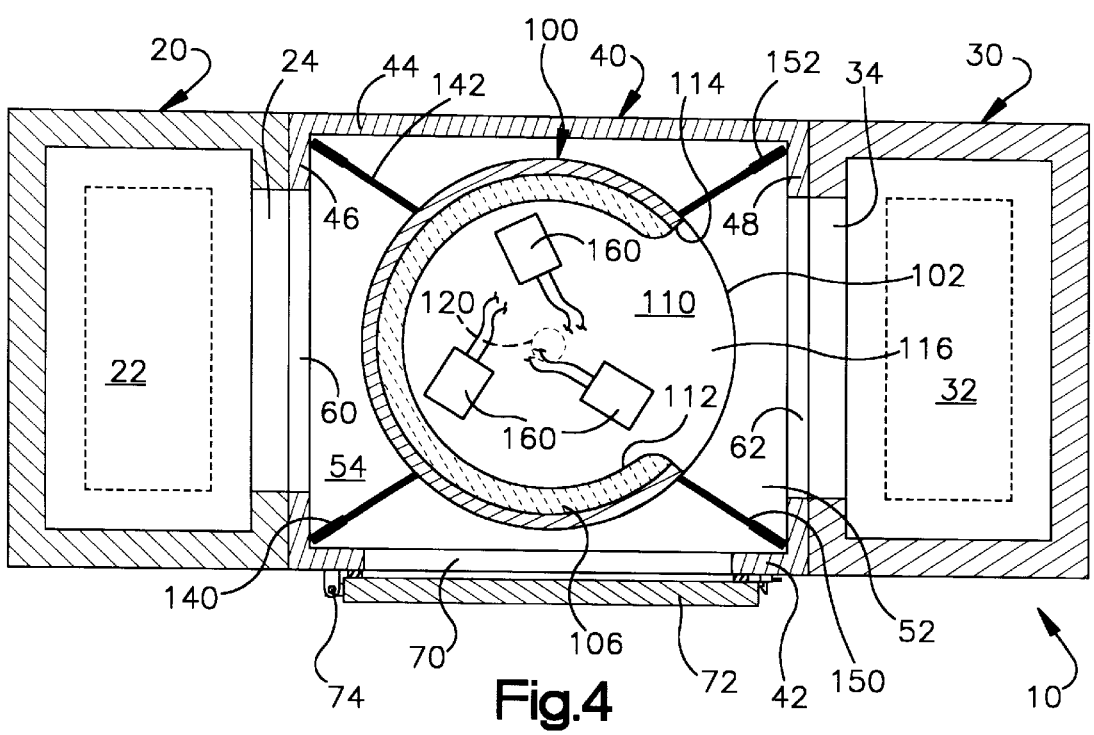

APPARATUS FOR TESTING ELECTRICAL COMPONENTS

TECHNICAL FIELD

The present invention is directed to an apparatus for testing electrical components, and is particularly directed to an apparatus for testing for the infiltration of moisture into electrical components due to environmental conditions.

BACKGROUND OF THE INVENTION

Vehicle components are subject to a variety of adverse environmental conditions, such as temperature extremes, precipitation, and salt. It is known to test vehicle electrical components and their associated connectors for resistance to such adverse environmental conditions. One known test involves temperature cycling of an electrical component and its electrical connector(s) between a relatively cold environment and a relatively hot environment to determine if condensation produced during the temperature cycling penetrates and adversely affects the connector and/or the electrical component. It is desirable to have a test apparatus which automates such a test and eliminates manual handling of the components during a test sequence.

SUMMARY OF THE INVENTION

The present invention is an apparatus for testing at least one article. The apparatus comprises a first chamber having a controllable first environment and a second chamber having a controllable second environment. One of the first and second environments is maintained at a relatively cold temperature and the other of the first and second environments is maintained at a relatively hot temperature with a relatively high humidity rate. An intermediate housing is connected between the first and second chambers. The intermediate housing defines a work space and includes a window which provides access to the work space. The intermediate housing includes a door for closing the window. A rotatable container is disposed in the work space. The container defines a test chamber in which the at least one article is placed.

The container is rotatable between a first position in which the test chamber is exposed to the first environment of the first chamber and is thermally insulated from the second environment of the second chamber, a second position in which the test chamber is exposed to the second environment of the second chamber and is thermally insulated from the first environment of the second chamber, and a third position in which the test chamber is accessible through the window in the intermediate housing and is thermally insulated from both of the first and second environments. The container is cycled between the first and second positions to allow for the development of moisture on the at least one article in the test chamber in order to determine if the moisture adversely affects the at least one article.

BRIEF DESCRIPTION OF THE DRAWINGS

The foregoing and other features of the present invention will become apparent to those skilled in the art to which the present invention relates upon reading the following description with reference to the accompanying drawings, wherein:

FIG. 3 is a view similar to FIG. 2 showing parts in different positions; and

FIG. 4 is a view similar to FIGS. 2 and 3 showing parts in different positions.

DESCRIPTION OF A PREFERRED EMBODIMENT

Figure 1:
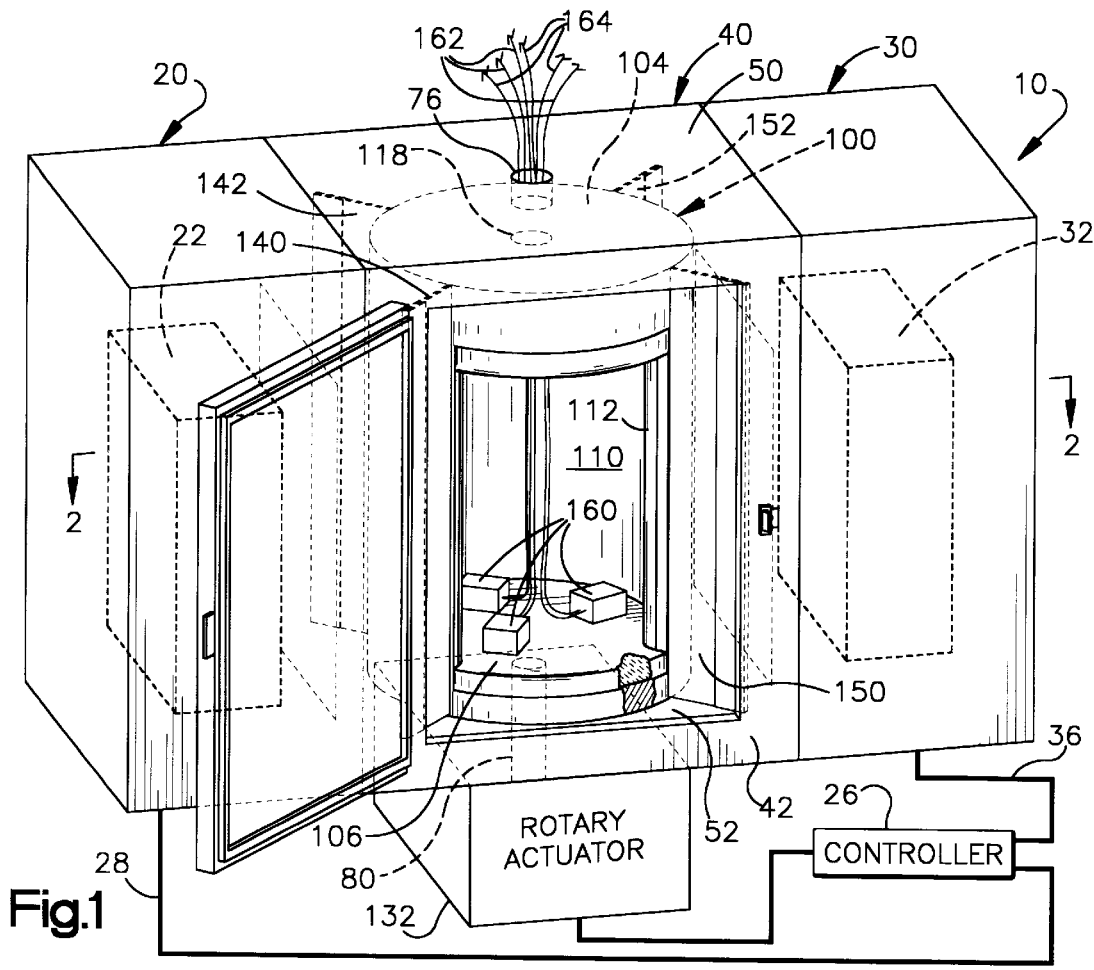
FIG. 1 is a schematic front view of a testing apparatus constructed in accordance with the present invention.

The present invention is directed to an apparatus for testing electrical components, and is particularly directed to an apparatus for testing for the infiltration of moisture into electrical components due to environmental conditions. As representative of the present invention, FIG. 1 illustrates an apparatus 10 including a first housing 20, a second housing 30, and an intermediate housing 40 connected between the first and second housings.

The first housing 20 defines a first chamber 22 within the first housing and preferably comprises a commercially available environmental chamber, such as the SM-8 model Thermotron brand chamber. As is known in the art, the environmental conditions within the first chamber 22 are controllable to be either hot, cold, humid, dry, or the like. The first housing 20 includes a generally rectangular first opening 24 (FIG. 2) which faces toward the intermediate housing 40. The first housing 20 is operatively electrically coupled to a programmable controller 26 by leads 28 shown schematically in FIG. 1.

The second housing 30 defines a second chamber 32 within the second housing and, as with the first housing 20, preferably comprises a commercially available environmental chamber, such as the SM-8 model Thermotron brand chamber. The environmental conditions within the second chamber 32 are also controllable to be either hot, cold, humid, dry, etc. The second housing 30 includes a generally rectangular second opening 34 which faces toward the intermediate housing 40. The second housing 30 is operatively electrically coupled to the programmable controller 26 by leads 36 shown schematically in FIG. 1.

The intermediate housing 40 (FIGS. 1 and 2) is a generally square metal structure having opposed first and second major side walls 42 and 44, opposed first and second minor side walls 46 and 48, an upper wall 50, and a lower wall 52 which together define a work space 54 inside the intermediate housing. The first minor side wall 46 of the intermediate housing 40 is secured to the first housing 20. A first window 60 is formed in the first minor side wall 46 and aligns with the first opening 24 in the first housing 20 to allow fluid communication between the first chamber 22 and the work space 54. The second minor side wall 48 is secured to the second housing 30. A second window 62 is formed in the second minor side wall 48 and aligns with the second opening 34 in the second housing 30 to allow fluid communication between the second chamber 32 and the work space 54.

The first major side wall 42 of the intermediate housing 40 has a third window 70 into the work space 54 inside the intermediate housing. A movable door 72 is attached to the first major side wall 42 by hinges 74 and is positionable to cover and close the third window 70. The upper wall 50 of the intermediate housing 40 includes a first aperture 76 for receiving electrical wires to be described later. The lower wall 52 of the intermediate housing includes a first passage 80 for receiving a shaft to be described later.

The apparatus 10 includes a rotatable container 100 located in the work space 54 inside the intermediate housing 40. The container 100 preferably comprises a generally cylindrical structure which is made of metal. The container 100 has a cylindrical side wall 102 and first and second end walls 104 and 106, respectively, which close the ends of the container. The side wall 102 and the end walls 104 and 106 together define a test chamber 110 inside the container 100. The test chamber 110 is lined with one or more layers of an insulating material 112. A cut-out 114 in the side wall 102 of the container 110 defines an opening 116 through the side wall into the test chamber 110.

The first end wall 104 of the container 110 extends adjacent and parallel to the upper wall 50 of the intermediate housing 40. The first end wall 104 includes a second aperture 118 which aligns with the first aperture 76 through the upper wall 50. The second end wall 106 of the container 100 extends adjacent and parallel to the lower wall 52 of the intermediate housing 40. The second end wall 106 includes a second passage 120 which aligns with the first passage 80 through the lower wall 52.

The container 100 is rotatably mounted on a shaft (not shown) which extends through the first and second passages 80 and 120. The shaft extends from a pneumatically operated rotary actuator 132, such as is manufactured by the PHD Company of Fort Wayne, Ind. The rotary actuator 132 is mounted underneath the intermediate housing 40 in a manner not shown. The rotary actuator 132 is operatively electrically coupled to the controller 26 as shown schematically in FIG. 1.

The rotary actuator 132 is operable to rotate the container 100 between first, second, and third positions. In the first position shown in FIG. 3, the opening 116 in the container 100 aligns with the first opening 24 in the first housing 20 and exposes the test chamber 110 to the environment inside the first chamber 22. In the second position shown in FIG. 4, the opening 116 in the container 100 aligns with the second opening 34 in the second housing 30 and exposes the test chamber 110 to the environment inside the second chamber 32. In the third position shown in FIG. 2, the opening 116 in the container 100 aligns with the third window 70 in the intermediate housing 40 to provide outside access to the test chamber 110.

A pair of insulating flaps 140 and 142 are located adjacent opposite lateral edges of the first window 60 in the intermediate housing 40. The flaps 140, 142 extend inward from the first minor side surface 46 of the intermediate housing 40 and slidingly engage the side wall 102 of the container 100. Each flap 140, 142 comprises two or more layers of a silicone sheet material. The flaps 140, 142 thermally insulate the work space 54 from the environment of the first chamber 22.

Similarly, a pair of insulating flaps 150 and 152 are located adjacent opposite lateral edges of the second window 62 in the intermediate housing 40. The flaps 140, 142 extend inward from the second minor side surface 48 of the intermediate housing 40 and slidingly engage the side wall 102 of the container 100. Each flap 150, 152 comprises two or more layers of a silicone sheet material. The flaps 150, 152 thermally insulate the work space 54 from the environment of the second chamber 32.

Figure 2:
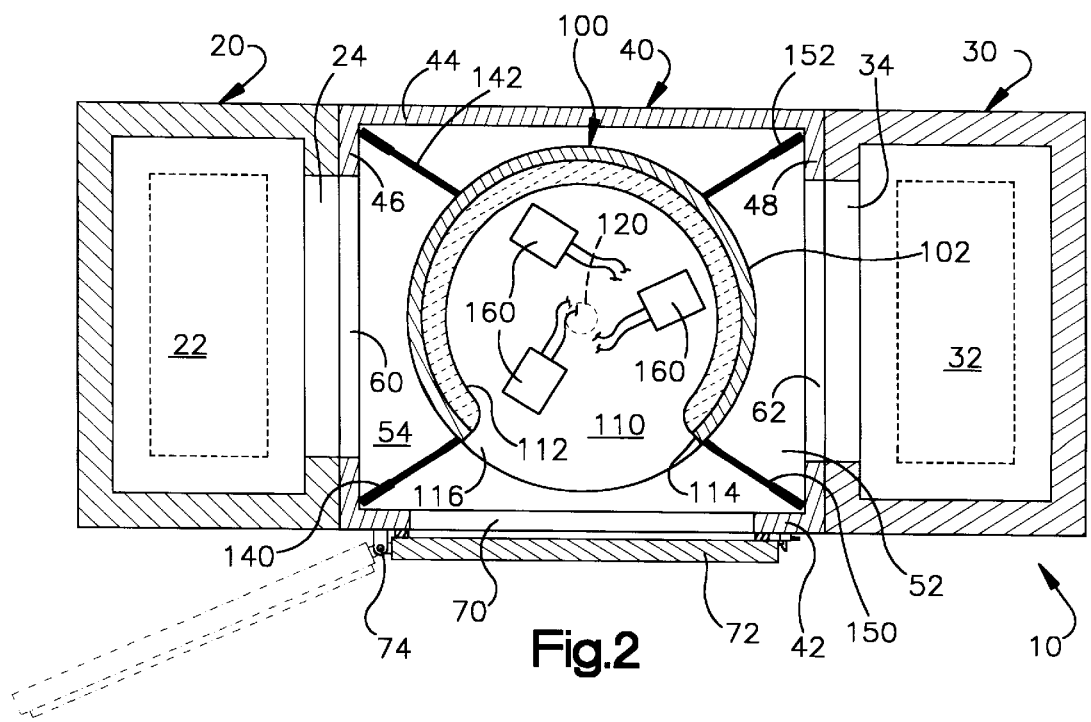
FIG. 2 is a schematic sectional view taken along line 2—2 in FIG. 1.

To use the apparatus 10, the container 100 is moved to the third position shown in FIG. 2 so that the opening 116 in the container is aligned with the third window 70 in the intermediate housing 40. The door 72 which covers the third window 70 is opened and articles 160 to be tested are placed into the test chamber 110 in the container 100. In accordance with one embodiment of the invention, the test articles 160 comprise a plurality of air bag modules. Electrical power wires 162 (FIG. 1) and instrumentation wires 164 extend from electrical connectors (not shown) on the air bag modules and are routed to the exterior of the apparatus 10 through the aligned passages 76 and 118 in the intermediate housing 40 and the container 100, respectively. The door 72 is then shut over the third window 70 to close the work space 54 in which the container 100 is located.

Next, the controller 26 is programmed with a predetermined test sequence which is designed to produce moisture in the form of condensation on the test articles 160 and their associated electrical connectors, such as would occur if a vehicle air conditioning system developed a leak in a hot environment. In accordance with a preferred embodiment of the invention, the controller 26 sets the temperature of the environment in the first chamber 22 at a relatively cold temperature of approximately −10° C. and sets the temperature of the environment inside the second chamber 32 at a relatively hot temperature of approximately 25° C. The environment inside the second chamber 32 is also set at a relatively high humidity rate of approximately 90%. In the third position of FIG. 2, the flaps 140, 142, 150 and 152 and the insulation 112 inside the test chamber 110 thermally insulate the test chamber from the respective environments of the first and second chambers 22 and 32.

Once the aforementioned environmental conditions are established in the first and second chambers 22 and 32, the controller 26 signals the rotary motor 132 to rotate the container 100 to the first position of FIG. 3 so that the test chamber 110 is exposed to the environment inside the first chamber 22. In this position, the flaps 140, 142 and the insulation 112 inside the container 100 thermally insulate the test chamber 110 from the environment inside the second chamber 32. The container 100 is maintained in the first position for a period of approximately one hour to allow for the test articles 160 in the test chamber 110 to attain a predetermined cold soak temperature.

When the one hour cold soak period is completed, the controller 26 signals the rotary actuator 132 to rotate the container 100 to the second position of FIG. 4 so that the test chamber 110 is exposed to the environment inside the second chamber 32. In this position, the flaps 150, 152 and the insulation 112 inside the container 100 thermally insulate the test chamber 110 from the environment inside the first chamber 22. The significant change in temperature and humidity from the environment of the first chamber 22 to the environment of the second chamber 32 causes moisture in the form of condensation to form on the test articles 160 and their associated electrical connectors. The container 100 is maintained in the second position for a period of approximately one hour to allow for the test articles 160 in the test chamber 110 to attain a predetermined hot soak temperature.

When the one hour hot soak period is finished, the test articles 160 have completed one test cycle in the test sequence. The controller 26 then signals the rotary actuator 132 to return the container 100 to the first position to begin another test cycle. Moisture which had formed on the test articles 160 as a result of the environmental conditions inside the second chamber 32 is now apt to freeze as a result of the environmental conditions inside the first chamber 22. If the moisture had undesirably penetrated into a test article 160, the expansion of the freezing moisture could lead to a problem with that test article 160 during the cold soak period or during the next hot soak period.

Preferably, twenty test cycles are done to complete an entire test sequence, during which time the continuity of electrical power to the test articles 160 and various other parameters of the test articles are monitored via the instrumentation wires 164. When twenty test cycles are completed, the controller signals the actuator 132 to return the container 100 to the third position of FIG. 2. The door 72 on the intermediate housing 40 is opened and the test articles 160 are removed from the test chamber 110 in the container 100 for visual inspection and various integrity checks.

The apparatus 10 described above provides a means for performing a moisture infiltration test on multiple electronic components at one time. Further, the apparatus 10 provides a means for performing the testing automatically and thereby eliminates any manual handling of the test articles 160 during a test sequence which is advantageous because manual handling could result in the loss of moisture accumulated on the test articles during the testing. Also, automation of the test process reduces the manpower requirements for performing the testing.

From the above description of the invention, those skilled in the art will perceive improvements, changes and modifications. Such improvements, changes and modifications within the skill of the art are intended to be covered by the appended claims.

Having described the invention, we claim:

1. An apparatus for testing at least one article, said apparatus comprising:
    a first chamber having a controllable first environment;
    a second chamber having a controllable second environment,
    one of said first and second environments being maintained at a relatively cold temperature and the other of said first and second environments being maintained at a relatively hot temperature with a relatively high humidity rate;
    an intermediate housing connected between said first and second chambers, said intermediate housing defining a work space and including a window which provides access to said work space, said intermediate housing including a door for closing said window; and
    a rotatable container disposed in said work space, said container defining a test chamber in which the at least one article is placed,
    said container being rotatable between a first position in which said test chamber is exposed to said first environment of said first chamber and is thermally insulated from said second environment of said second chamber, a second position in which said test chamber is exposed to said second environment of said second chamber and is thermally insulated from said first environment of said second chamber, and a third position in which said test chamber is accessible through said window in said intermediate housing and is thermally insulated from both of said first and second environments,
    said container being cycled between said first and second positions to allow for the development of moisture on the at least one article in said test chamber in order to determine if the moisture adversely affects the at least one article.

2. The apparatus of claim 1 wherein said intermediate housing includes means for thermally insulating said test chamber.

3. The apparatus of claim 2 further comprising means for controlling said first environment in said first chamber and means for controlling said second environment in said second chamber.

4. The apparatus of claim 3 further comprising means for rotating said container.

5. The apparatus of claim 4 further comprising a programmable controller operatively coupled to said means for rotating said container to control the cycling of said container between said first and second positions.

6. The apparatus of claim 5 wherein said programmable controller is operatively coupled with said means for controlling said first environment and is operatively coupled with said means for controlling said second environment.

7. The apparatus of claim 1 wherein said first chamber has a first opening facing toward said intermediate housing for providing fluid communication between said first environment and said work space.

8. The apparatus of claim 7 wherein said second chamber has a second opening facing toward said intermediate housing for providing fluid communication between said second environment and said work space.

9. The apparatus of claim 8 wherein said container has a third opening through which the at least one article is placed into said test chamber, said third opening being aligned with said first opening when said container is in said first position, said third opening being aligned with said second opening when said container is in said second position, said third opening being aligned with said window in said intermediate housing when said container is in said third position.

10. The apparatus of claim 1 wherein said first chamber has a first opening facing toward said intermediate housing for providing fluid communication between said first environment and said work space.

11. The apparatus of claim 10 wherein said second chamber has a second opening facing toward said intermediate housing for providing fluid communication between said second environment and said work space.

12. The apparatus of claim 11 wherein said container has a third opening through which the at least one article is placed into said test chamber, said third opening being aligned with said first opening in said first housing when said container is in said first position, said third opening being aligned with said second opening in said second housing when said container is in said second position, said third opening being aligned with said window in said intermediate housing when said container is in said third position.

13. The apparatus of claim 12 wherein said means for thermally insulating said work space includes a plurality of insulating flaps extending adjacent said first and second openings.

14. The apparatus of claim 13 wherein said container includes an aperture for receiving electrical wires associated with the at least one article in said test chamber.

15. An apparatus for testing at least one article, said apparatus comprising:
    a first housing defining a first chamber having a controllable first environment;
    a second housing defining a second chamber having a controllable second environment;
    an intermediate housing connected between said first and second housings, said intermediate housing defining a work space and including a window which provides access to said work space, said intermediate housing including a door for closing said window and means for thermally insulating said work space; and
    a rotatable container disposed in said work space, said container defining a test chamber in which the at least one article is placed,
    said container being rotatable between a first position in which said test chamber is exposed to said first environment of said first chamber and is thermally insulated from said second environment of said second chamber, a second position in which said test chamber is exposed to said second environment of said second chamber and is thermally insulated from said first environment of said second chamber, and a third position in which said test chamber is accessible through said window in said intermediate housing and is thermally insulated from both of said first and second environments.

16. The apparatus of claim 15 further comprising means for controlling said first environment in said first chamber and means for controlling said second environment in said second chamber.

17. The apparatus of claim 16 further comprising means for rotating said container.

18. The apparatus of claim 17 further comprising a programmable controller operatively coupled to said means for rotating said container to control the rotation of said container.

19. The apparatus of claim 18 wherein said programmable controller is operatively coupled with said means for controlling said first environment and with said means for controlling said second environment.

* * * * *

UNITED STATES PATENT AND TRADEMARK OFFICE
CERTIFICATE OF CORRECTION

PATENT NO. : 6,113,262
DATED      : September 5, 2000
INVENTOR(S): David Purola, David A. Klecha It is certified that error appears in the above-indentified patent and that said Letters Patent is hereby corrected as shown below:

Column 5, line 50, change "second" to "first"

Column 7, line 5, change "second" to "first"

Signed and Sealed this

First Day of May, 2001

Attest:

NICHOLAS P. GODICI

*Attesting Officer*   *Acting Director of the United States Patent and Trademark Office*